(12) United States Patent
Heath (10) Patent No.: US 10,357,014 B2
(45) Date of Patent: Jul. 23, 2019

(54) TOMATO HYBRID DR4299TC

(71) Applicant: Seminis Vegetable Seeds, Inc., St. Louis, MO (US)

(72) Inventor: Douglas William Heath, Rocklin, CA (US)

(73) Assignee: Seminis Vegetable Seeds, Inc., Woodland, CA (US)

(*) Notice: Subject to any disclaimer, the term of this patent is extended or adjusted under 35 U.S.C. 154(b) by 45 days.

(21) Appl. No.: 15/826,478

(22) Filed: Nov. 29, 2017

(65) Prior Publication Data

US 2018/0116155 A1    May 3, 2018

Related U.S. Application Data

(62) Division of application No. 15/159,779, filed on May 19, 2016, now Pat. No. 9,888,644, which is a division of application No. 14/480,494, filed on Sep. 8, 2014, now Pat. No. 9,370,145.

(51) Int. Cl.
*A01H 5/08*    (2018.01)
*A01H 6/82*    (2018.01)

(52) U.S. Cl.
CPC .............. *A01H 6/825* (2018.05); *A01H 5/08* (2013.01)

(58) Field of Classification Search
None
See application file for complete search history.

(56) References Cited

U.S. PATENT DOCUMENTS

| 7,816,583 | B2 | 10/2010 | Heath |   |
|---|---|---|---|---|
| 8,097,789 | B2 | 1/2012 | Heath |   |
| 8,097,790 | B2 | 1/2012 | Heath |   |
| 8,097,791 | B2 | 1/2012 | Heath |   |
| 9,888,644 | B2 * | 2/2018 | Heath | ...................... A01H 5/08 |
| 2009/0064367 | A1 | 3/2009 | Heath |   |
| 2012/0102586 | A1 | 4/2012 | Frantz |   |
| 2016/0000027 | A1 | 1/2016 | Heath |   |

OTHER PUBLICATIONS

Larkin et al., "Somaclonal Variation—a Novel Source of Variability from Cell Cultures for Plant Improvement," *Theor. Appl. Genet.* 60, 197-214; 1981.
Moose SP, Mumm RH., "Molecular plant breeding as the foundation for 21st century crop improvement", *Plant Physiol.*; 147(3):969-77; Jul. 2008.
Variety specific information as indicated in transmittal letter of May 28, 2015 Information Disclosure Statement for U.S. Appl. No. 14/480,494.

* cited by examiner

*Primary Examiner* — Phuong T Bui
(74) *Attorney, Agent, or Firm* — Dentons US LLP; Alissa Eagle (57) ABSTRACT

The invention provides seed and plants of tomato hybrid DR4299TC and the parent lines thereof. The invention thus relates to the plants, seeds and tissue cultures of tomato hybrid DR4299TC and the parent lines thereof, and to methods for producing a tomato plant produced by crossing such plants with themselves or with another tomato plant, such as a plant of another genotype. The invention further relates to seeds and plants produced by such crossing. The invention further relates to parts of such plants, including the fruit and gametes of such plants.

17 Claims, 1 Drawing Sheet

TOMATO HYBRID DR4299TC

This application is a divisional of U.S. patent application Ser. No. 15/159,779, filed May 19, 2016, now U.S. Pat. No. 9,888,644, which is a divisional of U.S. patent application Ser. No. 14/480,494, filed Sep. 8, 2014, now U.S. Pat. No. 9,370,145, the entire disclosures of which are incorporated herein by reference.

FIELD OF THE INVENTION

The present invention relates to the field of plant breeding and, more specifically, to the development of tomato hybrid DR4299TC and the inbred tomato lines CHI-A808018 and CHD-A808019.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a tomato plant of the hybrid designated DR4299TC, the tomato line CHI-A808018 or tomato line CHD-A808019. Also provided are tomato plants having all the physiological and morphological characteristics of such a plant. Parts of these tomato plants are also provided, for example, including pollen, an ovule, scion, a rootstock, a fruit, and a cell of the plant.

In another aspect of the invention, a plant of tomato hybrid DR4299TC and/or tomato lines CHI-A808018 and CHD-A808019 comprising an added heritable trait is provided. The heritable trait may comprise a genetic locus that is, for example, a dominant or recessive allele. In one embodiment of the invention, a plant of tomato hybrid DR4299TC and/or tomato lines CHI-A808018 and CHD-A808019 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of tomato hybrid DR4299TC and/or tomato lines CHI-A808018 and CHD-A808019. The tomato seed of the invention may be provided as an essentially homogeneous population of tomato seed of tomato hybrid DR4299TC and/or tomato lines CHI-A808018 and CHD-A808019. Essentially homogeneous populations of seed are generally free from substantial numbers of other seed. Therefore, in some embodiments, seed of hybrid DR4299TC and/or tomato lines CHI-A808018 and CHD-A808019 may be defined as forming at least about 97% of the total seed, including at least about 98%, 99% or more of the seed. The seed population may be separately grown to provide an essentially homogeneous population of tomato plants designated DR4299TC and/or tomato lines CHI-A808018 and CHD-A808019.

In yet another aspect of the invention, a tissue culture of regenerable cells of a tomato plant of hybrid DR4299TC and/or tomato lines CHI-A808018 and CHD-A808019 is provided. The tissue culture will preferably be capable of regenerating tomato plants capable of expressing all of the physiological and morphological characteristics of the starting plant, and of regenerating plants having substantially the same genotype as the starting plant. Examples of some of the physiological and morphological characteristics of the hybrid DR4299TC and/or tomato lines CHI-A808018 and CHD-A808019 include those traits set forth in the tables herein. The regenerable cells in such tissue cultures may be derived, for example, from embryos, meristems, cotyledons, pollen, leaves, anthers, roots, root tips, pistils, flowers, seed and stalks. Still further, the present invention provides tomato plants regenerated from a tissue culture of the invention, the plants having all the physiological and morphological characteristics of hybrid DR4299TC and/or tomato lines CHI-A808018 and CHD-A808019.

In still yet another aspect of the invention, processes are provided for producing tomato seeds, plants and fruit, which processes generally comprise crossing a first parent tomato plant with a second parent tomato plant, wherein at least one of the first or second parent tomato plants is a plant of tomato line CHI-A808018 or tomato line CHD-A808019. These processes may be further exemplified as processes for preparing hybrid tomato seed or plants, wherein a first tomato plant is crossed with a second tomato plant of a different, distinct genotype to provide a hybrid that has, as one of its parents, a plant of tomato line CHI-A808018 or tomato line CHD-A808019. In these processes, crossing will result in the production of seed. The seed production occurs regardless of whether the seed is collected or not.

In one embodiment of the invention, the first step in "crossing" comprises planting seeds of a first and second parent tomato plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent tomato plants into plants that bear flowers. A third step may comprise preventing self-pollination of the plants, such as by emasculating the flowers (i.e., killing or removing the pollen).

A fourth step for a hybrid cross may comprise cross-pollination between the first and second parent tomato plants. Yet another step comprises harvesting the seeds from at least one of the parent tomato plants. The harvested seed can be grown to produce a tomato plant or hybrid tomato plant.

The present invention also provides the tomato seeds and plants produced by a process that comprises crossing a first parent tomato plant with a second parent tomato plant, wherein at least one of the first or second parent tomato plants is a plant of tomato hybrid DR4299TC and/or tomato lines CHI-A808018 and CHD-A808019. In one embodiment of the invention, tomato seed and plants produced by the process are first generation ($F_1$) hybrid tomato seed and plants produced by crossing a plant in accordance with the invention with another, distinct plant. The present invention further contemplates plant parts of such an $F_1$ hybrid tomato plant, and methods of use thereof. Therefore, certain exemplary embodiments of the invention provide an $F_1$ hybrid tomato plant and seed thereof.

In still yet another aspect, the present invention provides a method of producing a plant derived from hybrid DR4299TC and/or tomato lines CHI-A808018 and CHD-A808019, the method comprising the steps of: (a) preparing a progeny plant derived from hybrid DR4299TC and/or tomato lines CHI-A808018 and CHD-A808019, wherein said preparing comprises crossing a plant of the hybrid DR4299TC and/or tomato lines CHI-A808018 and CHD-A808019 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid DR4299TC and/or tomato lines CHI-A808018 and CHD-A808019. The plant derived from hybrid DR4299TC and/or tomato lines CHI-A808018 and CHD-A808019 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid DR4299TC and/or tomato lines CHI-A808018 and CHD-A808019 is obtained which possesses some of the desirable traits of the line/hybrid as well as potentially other selected traits.

In certain embodiments, the present invention provides a method of producing food or feed comprising: (a) obtaining a plant of tomato hybrid DR4299TC and/or tomato lines CHI-A808018 and CHD-A808019, wherein the plant has been cultivated to maturity, and (b) collecting at least one tomato from the plant.

In still yet another aspect of the invention, the genetic complement of tomato hybrid DR4299TC and/or tomato lines CHI-A808018 and CHD-A808019 is provided. The phrase "genetic complement" is used to refer to the aggregate of nucleotide sequences, the expression of which sequences defines the phenotype of, in the present case, a tomato plant, or a cell or tissue of that plant. A genetic complement thus represents the genetic makeup of a cell, tissue or plant, and a hybrid genetic complement represents the genetic make up of a hybrid cell, tissue or plant. The invention thus provides tomato plant cells that have a genetic complement in accordance with the tomato plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid DR4299TC and/or tomato lines CHI-A808018 and CHD-A808019 could be identified by any of the many well known techniques such as, for example, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In still yet another aspect, the present invention provides hybrid genetic complements, as represented by tomato plant cells, tissues, plants, and seeds, formed by the combination of a haploid genetic complement of a tomato plant of the invention with a haploid genetic complement of a second tomato plant, preferably, another, distinct tomato plant. In another aspect, the present invention provides a tomato plant regenerated from a tissue culture that comprises a hybrid genetic complement of this invention.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of tomato hybrid DR4299TC, tomato line CHI-A808018 and tomato line CHD-A808019.

Tomato hybrid DR4299TC, also known as PX 01544299, has orange fruit color around 7-15 g in size and very good brix levels comparable to BS 01543756. The plant is moderately vigorous and is suited to glass house production due to its TMV resistance.

A. Origin and Breeding History of Tomato Hybrid DR4299TC

The parents of hybrid DR4299TC are CHI-A808018 and CHD-A808019. These parents were created as follows:

Both parental inbred lines were derived from the origin CHI-A806033/CHD-15-2059. Parent line CHI-A808018 is indeterminate and carries resistance to TOMV, Aa and BSK and carries the tangerine allele at the tangerine fruit color locus. Parent line CHD-A808019 is determinate and carries the tangerine allele at the tangerine fruit color locus.

The parent lines are uniform and stable, as is a hybrid produced therefrom. A small percentage of variants can occur within commercially acceptable limits for almost any characteristic during the course of repeated multiplication. However no variants are expected.

B. Physiological and Morphological Characteristics of Tomato Hybrid DR4299TC, Tomato Line CHI-A808018 and Tomato Line CHD-A808019

In accordance with one aspect of the present invention, there is provided a plant having the physiological and morphological characteristics of tomato hybrid DR4299TC and the parent lines thereof. A description of the physiological and morphological characteristics of such plants is presented in Tables 1-3.

TABLE 1

Physiological and Morphological Characteristics of Hybrid DR4299TC

| Characteristic | DR4299TC | Comparison: BS 01543756 |
| --- | --- | --- |
| 1. Seedling | | |
| anthocyanin in hypocotyl of 2-15 cm seedling | present | present |
| habit of 3-4 week old seedling | normal | normal |
| 2. Mature Plant | | |
| height | 96.9 cm | 94.6 cm |
| growth type | indeterminate | indeterminate |
| plant: number of inflorescences on main stem (side shoots to be removed) | many | many |
| form | lax, open | lax, open |
| size of canopy (compared to others of similar type) | large | large |
| habit | sprawling | sprawling |
| stem: anthocyanin coloration | absent or very weak | absent or very weak |
| 3. Stem | | |
| branching | profuse | profuse |
| branching at cotyledon or first leafy node | present | present |
| number of nodes between first inflorescence | 7 to 10 | 4 to 7 |
| number of nodes between early ($1^{st}$ to $2^{nd}$, $2^{nd}$ to $3^{rd}$) inflorescences | 1 to 4 | 1 to 4 |
| number of nodes between later developing inflorescences | 10 or more | 7 to 10 |
| pubescence on younger stems | moderately hairy | moderately hairy |
| 4. Leaf | | |
| type (mature leaf beneath the $3^{rd}$ inflorescence) | tomato | tomato |
| type of blade | pinnate | pinnate |
| margins of major leaflets (mature leaf beneath the $3^{rd}$ inflorescence) | shallowly toothed or scalloped | shallowly toothed |
| marginal rolling or wiltiness (mature leaf beneath the $3^{rd}$ inflorescence) | slight | slight |
| onset of leaflet rolling | late season | mid season |
| surface of major leaflets (mature leaf beneath the $3^{rd}$ inflorescence) | smooth | rugose |
| pubescence (mature leaf beneath the $3^{rd}$ inflorescence) | normal | normal |
| attitude (in middle third of plant) | semi-erect | semi-erect |
| length | short | medium |
| width | narrow | narrow |
| size of leaflets | very small | small |
| intensity of green color | dark | dark |
| glossiness | medium | medium |

TABLE 1-continued

Physiological and Morphological Characteristics of Hybrid DR4299TC

| Characteristic | DR4299TC | Comparison: BS 01543756 |
|---|---|---|
| blistering | medium | medium |
| attitude of petiole of leaflet in relation to main axis | horizontal | semi-drooping |
| 5. Inflorescence | | |
| inflorescence type | mainly multiparious | mainly multiparious |
| type (3$^{rd}$ inflorescence) | compound (much branched) | compound |
| average number of flowers in inflorescence (3$^{rd}$ inflorescence) | 40.4 | 62.6 |
| leafy or "running" inflorescence (3$^{rd}$ inflorescence) | absent | frequent |
| 6. Flower | | |
| color | yellow | yellow |
| calyx | normal (lobes awl shaped) | normal |
| calyx-lobes | shorter than corolla | shorter than corolla |
| corolla color | yellow | yellow |
| style pubescence | dense | sparse |
| anthers | all fused into tube | all fused into tube |
| fasciation (1$^{st}$ flower of 2$^{nd}$ or 3$^{rd}$ inflorescence) | absent | absent |
| 7. Fruit | | |
| peduncle: abscission layer | present | present |
| surface | smooth | smooth |
| base color (mature-green stage) | light gray-green | light gray-green |
| pattern (mature-green stage) | green-shouldered | uniform green |
| shoulder color if different from base | dark green | dark green |
| green shoulder (before maturity) | present | present |
| extent of green shoulder (before maturity) | medium | medium |
| intensity of green color of shoulder (before maturity) | medium | medium |
| intensity of green color excluding shoulder (before maturity) | light | light |
| green stripes (before maturity) | absent | absent |
| size | very small | very small |
| ratio length/diameter | moderately compressed | very small |
| shape in longitudinal section | pyriform | ovate |
| shape of transverse/cross section (3rd fruit of 2nd or 3rd cluster) | flattened | flattened |
| shape of stem end (3rd fruit of 2nd or 3rd cluster) | flat | flat |
| shape of blossom end | flat | flat |
| shape of pistil scar (3rd fruit of 2nd or 3rd cluster) | dot | dot |
| ribbing at peduncle end | absent or very weak | absent or very weak |
| depression at peduncle end | absent or very weak | absent or very weak |
| size of stem/peduncle scar | very small | very small |
| size of blossom scar | very small | very small |
| point of detachment of fruit at harvest (3rd fruit of 2nd or 3rd cluster) | at calyx attachment | at pedicel joint |
| length of mature fruit (3rd fruit of 2nd or 3rd cluster) | 27.8 mm | 26.8 mm |
| diameter of fruit (3rd fruit of 2nd or 3rd cluster) | 18.7 mm | 17.9 mm |
| weight of mature fruit (3rd fruit of 2nd or 3rd cluster) | 5.8 grams | 5.3 grams |
| core | present | present |
| diameter of core in cross section in relation to total diameter | very small | very small |
| number of locules | two | two |
| number of locules *refer to TG for pictures of locules | two and three | two and three |
| color, full ripe | orange | orange |
| color (at maturity) | orange | orange |
| flesh color, full-ripe | orange | uniform |
| color of flesh (at maturity) | orange | orange |
| glossiness of skin | strong | strong |
| flesh color | uniform | uniform |
| locular gel color of table-ripe fruit | yellow | yellow |
| firmness | medium | medium |
| shelf life | medium | medium |
| time of flowering | early | early |
| time of maturity | early | early |
| ripening | uniform | uniform |

TABLE 1-continued

Physiological and Morphological Characteristics of Hybrid DR4299TC

| Characteristic | DR4299TC | Comparison: BS 01543756 |
|---|---|---|
| ripening | uniformity | uniformity |
| epidermis color | yellow | yellow |
| epidermis | easy-peel | easy-peel |
| epidermis texture | tender | tender |
| thickness of pericarp | thin | thin |
| sensitivity to silvering | insensitive | insensitive |
| 11. Phenology | | |
| seeding to 50% flow (1 open on 50% of plants) | 53 | 53 |
| seeding to once over harvest (if applicable) | 105 | 105 |
| fruiting season | medium | medium |
| 12. Adaptation | | |
| culture | field | field |
| 10. Chemistry and Composition of Full-Ripe Fruits | | |
| pH | 4.3 | 4.4 |
| Titratable acidity, as % citric | 0.56 | 0.52 |
| Total solids (dry matter, seeds and skin removed) | 9.8 | 10.4 |
| Soluble solids as °Brix | 8.7 | 8.6 |

*These are typical values. Values may vary due to environment. Other values that are substantially equivalent are also within the scope of the invention.

TABLE 2

Physiological and Morphological Characteristics of Line CHI-A808018

| Characteristic | CHI-A808018 | Comparison: BS 01543756 |
|---|---|---|
| 1. Seedling | | |
| anthocyanin in hypocotyl of 2-15 cm seedling | present | present |
| habit of 3-4 week old seedling | normal | normal |
| 2. Mature Plant | | |
| height | 102.9 cm | 94.6 cm |
| growth type | indeterminate | indeterminate |
| form | lax, open | lax, open |
| size of canopy (compared to others of similar type) | small | large |
| habit | sprawling | sprawling |
| stem: anthocyanin coloration | medium | absent or very weak |
| stem: length of internode (only indeterminate growth type varieties) | medium | |
| height (only indeterminate growth type varieties) | medium | |
| 3. Stem | | |
| branching | intermediate | profuse |
| branching at cotyledon or first leafy node | present | present |
| number of nodes between first inflorescence | 4 to 7 | 4 to 7 |
| number of nodes between early ($1^{st}$ to $2^{nd}$, $2^{nd}$ to $3^{rd}$) inflorescences | 1 to 4 | 1 to 4 |
| number of nodes between later developing inflorescences | 7 to 10 | 7 to 10 |
| pubescence on younger stems | sparsely hairy (scattered long hairs) | moderately hairy |
| 4. Leaf | | |
| type (mature leaf beneath the $3^{rd}$ inflorescence) | tomato | tomato |
| type of blade | pinnate | pinnate |
| margins of major leaflets (mature leaf beneath the $3^{rd}$ inflorescence) | shallowly toothed or scalloped | shallowly toothed |
| marginal rolling or wiltness (mature leaf beneath the $3^{rd}$ inflorescence) | slight | slight |
| onset of leaflet rolling | mid season | mid season |
| surface of major leaflets (mature leaf beneath the $3^{rd}$ inflorescence) | smooth | rugose |
| pubescence (mature leaf beneath the $3^{rd}$ inflorescence) | normal | normal |
| attitude (in middle third of plant) | horizontal | semi-erect |
| length | medium | medium |
| width | narrow | narrow |
| size of leaflets | very small | small |

TABLE 2-continued

Physiological and Morphological Characteristics of Line CHI-A808018

| Characteristic | CHI-A808018 | Comparison: BS 01543756 |
|---|---|---|
| intensity of green color | dark | dark |
| glossiness | strong | medium |
| blistering | medium | medium |
| attitude of petiole of leaflet in relation to main axis | semi-erect | semi-drooping |
| 5. Inflorescence | | |
| inflorescence type | mainly uniparous | mainly multiparous |
| type ($3^{rd}$ inflorescence) | forked (2 major axes) | compound |
| average number of flowers in inflorescence ($3^{rd}$ inflorescence) | 35.2 | 62.6 |
| leafy or "running" inflorescence ($3^{rd}$ inflorescence) | absent | frequent |
| 6. Flower | | |
| color | yellow | yellow |
| calyx | normal (lobes awl shaped) | normal |
| calyx-lobes | shorter than corolla | shorter than corolla |
| corolla color | yellow | yellow |
| style pubescence | dense | sparse |
| anthers | all fused into tube | all fused into tube |
| fasciation ($1^{st}$ flower of $2^{nd}$ or $3^{rd}$ inflorescence) | absent | absent |
| 7. Fruit | | |
| peduncle: abscission layer | present | present |
| surface | smooth | smooth |
| base color (mature-green stage) | light gray-green | light gray-green |
| pattern (mature-green stage) | uniform green | uniform green |
| green shoulder (before maturity) | absent | present |
| intensity of green color excluding shoulder (before maturity) | light | light |
| size | very small | very small |
| ratio length/diameter | medium | very small |
| shape in longitudinal section | pyriform | ovate |
| shape of transverse/cross section (3rd fruit of 2nd or 3rd cluster) | round | flattened |
| shape of stem end (3rd fruit of 2nd or 3rd cluster) | flat | flat |
| shape of blossom end | flat to pointed | flat |
| shape of pistil scar (3rd fruit of 2nd or 3rd cluster) | dot | dot |
| ribbing at peduncle end | absent or very weak | absent or very weak |
| depression at peduncle end | absent or very weak | absent or very weak |
| size of stem/peduncle scar | very small | very small |
| size of blossom scar | very small | very small |
| point of detachment of fruit at harvest (3rd fruit of 2nd or 3rd cluster) | at calyx attachment | at pedicel joint |
| length of mature fruit (3rd fruit of 2nd or 3rd cluster) | 31.0 mm | 26.8 mm |
| diameter of fruit (3rd fruit of 2nd or 3rd cluster) | 17.0 mm | 17.9 mm |
| weight of mature fruit (3rd fruit of 2nd or 3rd cluster) | 6.5 grams | 5.3 grams |
| core | present | present |
| diameter of core in cross section in relation to total diameter | small | very small |
| number of locules | three and four | two |
| number of locules | three and four | two and three |
| *refer to TG for pictures of locules | | |
| color, full ripe | orange | orange |
| color (at maturity) | orange | orange |
| flesh color, full-ripe | orange | uniform |
| color of flesh (at maturity) | orange | orange |
| glossiness of skin | strong | strong |
| flesh color | uniform | uniform |
| locular gel color of table-ripe fruit | yellow | yellow |
| firmness | medium | medium |
| shelf life | medium | medium |
| time of flowering | early | early |
| time of maturity | medium | early |
| ripening | uniform | uniform |
| ripening | uniformity | uniformity |
| epidermis color | yellow | yellow |

TABLE 2-continued

Physiological and Morphological Characteristics of Line CHI-A808018

| Characteristic | CHI-A808018 | Comparison: BS 01543756 |
|---|---|---|
| epidermis | easy-peel | easy-peel |
| epidermis texture | tender | tender |
| thickness of pericarp | very thin | thin |
| sensitivity to silvering | insensitive | insensitive |
| 11. Phenology | | |
| seeding to 50% flow (1 open on 50% of plants) | 52 | 53 |
| seeding to once over harvest (if applicable) | 102 | 105 |
| fruiting season | medium | medium |
| 12. Adaptation | | |
| culture | field | field |
| 10. Chemistry and Composition of Full-Ripe Fruits | | |
| pH | 4.5 | 4.4 |
| Titratable acidity, as % citric | 0.39 | 0.52 |
| Total solids (dry matter, seeds and skin removed) | 10.3 | 10.4 |
| Soluble solids as °Brix | 9.3 | 8.6 |

*These are typical values. Values may vary due to environment. Other values that are substantially equivalent are also within the scope of the invention.

TABLE 3

Physiological and Morphological Characteristics of Line CHD-A808019

| Characteristic | CHD-A808019 | Comparison: BS 01543756 |
|---|---|---|
| 1. Seedling | | |
| anthocyanin in hypocotyl of 2-15 cm seedling | present | present |
| habit of 3-4 week old seedling | normal | normal |
| 2. Mature Plant | | |
| height | 49.9 cm | 94.6 cm |
| growth type | determinate | indeterminate |
| plant: number of inflorescences on main stem (side shoots to be removed) | many | many |
| form | lax, open | lax, open |
| size of canopy (compared to others of similar type) | large | large |
| habit | sprawling | sprawling |
| stem: anthocyanin coloration | absent or very weak | absent or very weak |
| 3. Stem | | |
| branching | profuse | profuse |
| branching at cotyledon or first leafy node | present | present |
| number of nodes between first inflorescence | 4 to 7 | 4 to 7 |
| number of nodes between early ($1^{st}$ to $2^{nd}$, $2^{nd}$ to $3^{rd}$) inflorescences | 1 to 4 | 1 to 4 |
| number of nodes between later developing inflorescences | 1 to 4 | 7 to 10 |
| pubescence on younger stems | sparsely hairy (scattered long hairs) | moderately hairy |
| 4. Leaf | | |
| type (mature leaf beneath the $3^{rd}$ inflorescence) | tomato | tomato |
| type of blade | pinnate | pinnate |
| margins of major leaflets (mature leaf beneath the $3^{rd}$ inflorescence) | shallowly toothed or scalloped | shallowly toothed |
| marginal rolling or wiltness (mature leaf beneath the $3^{rd}$ inflorescence) | slight | slight |
| onset of leaflet rolling | mid season | mid season |
| surface of major leaflets (mature leaf beneath the $3^{rd}$ inflorescence) | rugose (bumpy or veiny) | rugose |
| pubescence (mature leaf beneath the $3^{rd}$ inflorescence) | normal | normal |
| attitude (in middle third of plant) | horizontal | semi-erect |
| length | medium | medium |
| width | narrow | narrow |
| size of leaflets | medium | small |
| intensity of green color | dark | dark |

TABLE 3-continued

Physiological and Morphological Characteristics of Line CHD-A808019

| Characteristic | CHD-A808019 | Comparison: BS 01543756 |
|---|---|---|
| glossiness | medium | medium |
| blistering | medium | medium |
| attitude of petiole of leaflet in relation to main axis | horizontal | semi-drooping |
| 5. Inflorescence | | |
| inflorescence type | mainly multiparious compound (much branched) | mainly multiparious compound |
| type ($3^{rd}$ inflorescence) | | |
| average number of flowers in inflorescence ($3^{rd}$ inflorescence) | 49.8 | 62.6 |
| leafy or "running" inflorescence ($3^{rd}$ inflorescence) | frequent | frequent |
| 6. Flower | | |
| color | yellow | yellow |
| calyx | normal (lobes awl shaped) | normal |
| calyx-lobes | shorter than corolla | shorter than corolla |
| corolla color | yellow | yellow |
| style pubescence | dense | sparse |
| anthers | all fused into tube | all fused into tube |
| fasciation ($1^{st}$ flower of $2^{nd}$ or $3^{rd}$ inflorescence) | absent | absent |
| 7. Fruit | | |
| peduncle: abscission layer | present (pedicellate) | present |
| pedicel: length (only varieties with peduncle abscission layer present) | long | medium |
| surface | smooth | smooth |
| base color (mature-green stage) | light gray-green | light gray-green |
| pattern (mature-green stage) | uniform green | uniform green |
| shoulder color if different from base | grey green | dark green |
| green shoulder (before maturity) | present | present |
| extent of green shoulder (before maturity) | medium | medium |
| intensity of green color of shoulder (before maturity) | dark | medium |
| intensity of green color excluding shoulder (before maturity) | light | light |
| green stripes (before maturity) | absent | absent |
| size | very small | very small |
| ratio length/diameter | moderately compressed | very small |
| shape in longitudinal section | ovate | ovate |
| shape of transverse/cross section (3rd fruit of 2nd or 3rd cluster) | flattened | flattened |
| shape of stem end (3rd fruit of 2nd or 3rd cluster) | flat | flat |
| shape of blossom end | flat to pointed | flat |
| shape of pistil scar (3rd fruit of 2nd or 3rd cluster) | dot | dot |
| ribbing at peduncle end | absent or very weak | absent or very weak |
| depression at peduncle end | absent or very weak | absent or very weak |
| size of stem/peduncle scar | very small | very small |
| size of blossom scar | very small | very small |
| point of detachment of fruit at harvest (3rd fruit of 2nd or 3rd cluster) | at pedicel joint | at pedicel joint |
| length of pedicel (3rd fruit of 2nd or 3rd cluster) | 8.9 mm | 7.8 mm |
| length of mature fruit (3rd fruit of 2nd or 3rd cluster) | 28.7 mm | 26.8 mm |
| diameter of fruit (3rd fruit of 2nd or 3rd cluster) | 18.2 mm | 17.9 mm |
| weight of mature fruit (3rd fruit of 2nd or 3rd cluster) | 6.6 grams | 5.3 grams |
| core | present | present |
| diameter of core in cross section in relation to total diameter | very small | very small |
| number of locules | two | two |
| number of locules | two and three | two and three |
| *refer to TG for pictures of locules | | |
| color, full ripe | orange | orange |
| color (at maturity) | orange | orange |
| flesh color, full-ripe | orange | uniform |
| color of flesh (at maturity) | orange | orange |
| glossiness of skin | strong | strong |
| flesh color | uniform | uniform |
| locular gel color of table-ripe fruit | yellow | yellow |

TABLE 3-continued

Physiological and Morphological Characteristics of Line CHD-A808019

| Characteristic | CHD-A808019 | Comparison: BS 01543756 |
|---|---|---|
| firmness | medium | medium |
| shelf life | medium | medium |
| time of flowering | early | early |
| time of maturity | very early | early |
| ripening | uniform | uniform |
| ripening | uniformity | uniformity |
| epidermis color | yellow | yellow |
| epidermis | easy-peel | easy-peel |
| epidermis texture | tender | tender |
| thickness of pericarp | thin | thin |
| sensitivity to silvering | insensitive | insensitive |
| 11. Phenology | | |
| seeding to 50% flow (1 open on 50% of plants) | 53 | 53 |
| seeding to once over harvest (if applicable) | 104 | 105 |
| fruiting season | medium | medium |
| 12. Adaptation | | |
| culture | field | field |
| 10. Chemistry and Composition of Full-Ripe Fruits | | |
| pH | 4.2 | 4.4 |
| Titratable acidity, as % citric | 0.58 | 0.52 |
| Total solids (dry matter, seeds and skin removed) | 10.1 | 10.4 |
| Soluble solids as °Brix | 8.9 | 8.6 |

*These are typical values. Values may vary due to environment. Other values that are substantially equivalent are also within the scope of the invention.

C. Breeding Tomato Plants

One aspect of the current invention concerns methods for producing seed of tomato hybrid DR4299TC involving crossing tomato lines CHI-A808018 and CHD-A808019. Alternatively, in other embodiments of the invention, hybrid DR4299TC, line CHI-A808018, or line CHD-A808019 may be crossed with itself or with any second plant. Such methods can be used for propagation of hybrid DR4299TC and/or the tomato lines CHI-A808018 and CHD-A808019, or can be used to produce plants that are derived from hybrid DR4299TC and/or the tomato lines CHI-A808018 and CHD-A808019. Plants derived from hybrid DR4299TC and/or the tomato lines CHI-A808018 and CHD-A808019 may be used, in certain embodiments, for the development of new tomato varieties.

The development of new varieties using one or more starting varieties is well known in the art. In accordance with the invention, novel varieties may be created by crossing hybrid DR4299TC followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines based on the elite nature of the genetic background of the plants. In selecting a second plant to cross with DR4299TC and/or tomato lines CHI-A808018 and CHD-A808019 for the purpose of developing novel tomato lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of tomato plants developed by this invention.

D. Performance Characteristics

Figure 1:
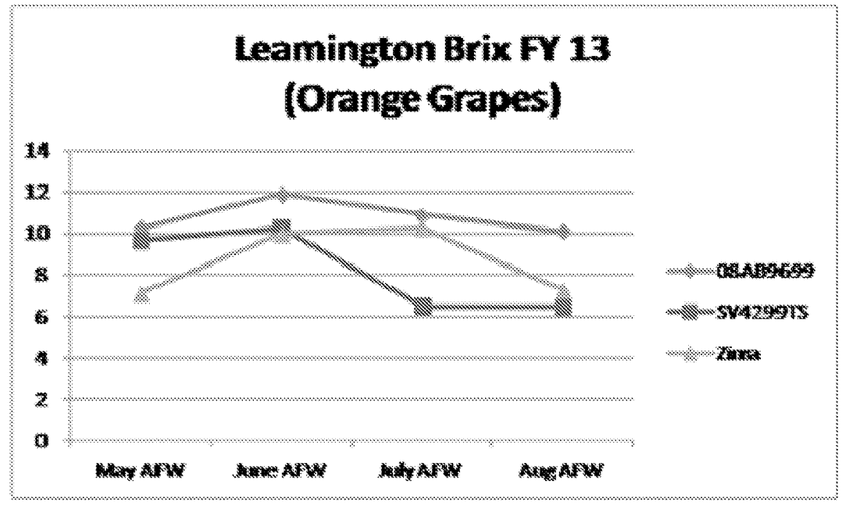
FIG. 1: Performance data of hybrid DR4299TC and Comparative Variety

As described above, hybrid DR4299TC exhibits desirable traits, as conferred by tomato lines CHI-A808018 and CHD-A808019. The performance characteristics of hybrid DR4299TC and tomato lines CHI-A808018 and CHD-A808019 were the subject of an objective analysis of the performance traits is presented in FIG. 1.

E. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those tomato plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental tomato plant which contributes the locus for the desired characteristic is termed the nonrecurrent or donor parent. This terminology refers to the fact that the nonrecurrent parent is used one time in the backcross protocol and therefore does not recur. The parental tomato plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a tomato plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny tomato plants of a backcross in which a plant described herein is the recurrent parent comprise (i) the desired trait from the non-recurrent parent and (ii) all of the physiological and morphological characteristics of tomato the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

F. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio-Technology*, 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio/Technology*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107: 462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including in monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S); 1 the nopaline synthase promoter (An et al., *Plant Physiol.*, 88:547, 1988); the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., *Plant Physiol.,* 88:965, 1988), (2) light (e.g., pea rbcS-3A promoter, Kuhlemeier et al., *Plant Cell,* 1:471, 1989; maize rbcS promoter, Schaffner and Sheen, *Plant Cell,* 3:997, 1991; or chlorophyll a/b-binding protein promoter, Simpson et al., *EMBO J.,* 4:2723, 1985), (3) hormones, such as abscisic acid (Marcotte et al., *Plant Cell,* 1:969, 1989), (4) wounding (e.g., wunl, Siebertz et al., *Plant Cell,* 1:961, 1989); or (5) chemicals such as methyl jasmonate, salicylic acid, or Safener. It may also be advantageous to employ organ-specific promoters (e.g., Roshal et al., *EMBO J.,* 6:1155, 1987; Schernthaner et al., *EMBO J.,* 7:1249, 1988; Bustos et al., *Plant Cell,* 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a tomato plant according to the invention. Non-limiting examples of particular genes and corresponding phenotypes one may choose to introduce into a tomato plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.,* 9:207, 1991). The RNA could also be a catalytic RNA molecule (i.e., a ribozyme) engineered to cleave a desired endogenous mRNA product (see for example, Gibson and Shillito, *Mol. Biotech.,* 7:125, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Royal Horticultural Society (RHS) color chart value: The RHS color chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a tomato variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a tomato plant by transformation.

H. Deposit Information

A deposit of tomato hybrid DR4299TC and inbred parent lines CHI-A808018 and CHD-A808019, disclosed above and recited in the claims, has been made with the American Type Culture Collection (ATCC), 10801 University Blvd., Manassas, Va. 20110-2209. The date of deposit was Jul. 30, 2014. The accession numbers for those deposited seeds of tomato hybrid DR4299TC and inbred parent lines CHI-A808018 and CHD-A808019, are ATCC Accession No. PTA-121437, ATCC Accession No. PTA-121436, and ATCC Accession No. PTA-121435, respectively. Upon issuance of a patent, all restrictions upon the deposits will be removed, and the deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A tomato plant of tomato hybrid DR4299TC, a sample of seed of said hybrid DR4299TC having been deposited under ATCC Accession Number PTA-121437.

2. A seed that produces the plant of claim 1.

3. A tissue culture of regenerable cells of the plant of claim 1.

4. The tissue culture according to claim 3, comprising cells or protoplasts from a plant part selected from the group consisting of embryos, meristems, cotyledons, pollen, leaves, anthers, roots, root tips, pistil, flower, seed and stalks, wherein said cells or protoplasts comprise a cell or protoplast of said tomato hybrid DR4299TC.

5. A tomato plant regenerated from the tissue culture of claim 3, wherein said plant has all of the morphological and physiological characteristics of tomato hybrid DR4299TC.

6. A method of vegetatively propagating the tomato plant of claim 1, the method comprising the steps of:
(a) collecting tissue capable of being propagated from the plant according to claim 1;
(b) propagating a tomato plant from said tissue.

7. A method of producing a tomato plant comprising an added trait, the method comprising introducing a transgene conferring the trait into the plant according to claim 1.

8. A tomato plant produced by the method of claim 7, wherein said plant comprises the trait and otherwise comprises all the physiological and morphological characteristics of hybrid DR4299TC.

9. A tomato plant of tomato hybrid DR4299TC, a sample of seed of said hybrid DR4299TC having been deposited under ATCC Accession Number PTA-121437, further comprising a transgene.

10. The plant of claim 9, wherein the transgene confers a trait selected from the group consisting of male sterility, herbicide tolerance, insect resistance, pest resistance, disease resistance, modified fatty acid metabolism, environmental stress tolerance, modified carbohydrate metabolism and modified protein metabolism.

11. A tomato plant of tomato hybrid DR4299TC, a sample of seed of said hybrid DR4299TC having been deposited under ATCC Accession Number PTA-121437, further comprising a single locus conversion.

12. The plant of claim 11, wherein the single locus conversion confers a trait selected from the group consisting of male sterility, herbicide tolerance, insect resistance, pest resistance, disease resistance, modified fatty acid metabolism, environmental stress tolerance, modified carbohydrate metabolism and modified protein metabolism.

13. A method for producing a seed of a tomato plant derived from tomato hybrid DR4299TC, the method comprising the steps of:
(a) crossing the tomato plant according to claim 1 with itself or a second tomato plant; and
(b) allowing seed of a hybrid DR4299TC-derived tomato plant to form.

14. The method of claim 13, further comprising the steps of:
(c) selfing a plant grown from said hybrid DR4299TC-derived tomato seed to yield additional hybrid DR4299TC-derived tomato seed;
(d) growing said additional hybrid DR4299TC-derived tomato seed of step (c) to yield additional hybrid DR4299TC-derived tomato plants; and
(e) repeating the selfing and growing steps of (c) and (d) to generate at least a first further hybrid DR4299TC-derived tomato plant.

15. The method of claim 14, further comprising:
(f) crossing the further hybrid DR4299TC derived tomato plant with a second tomato plant to produce seed of a hybrid progeny plant.

16. A plant part of the plant of claim 1, wherein the plant part comprises a cell of said hybrid DR4299TC.

17. A method of producing a tomato fruit, the method comprising:
   (a) obtaining the plant according to claim 1, wherein the plant has been cultivated to maturity; and
   (b) collecting a tomato fruit from the plant.

\* \* \* \* \*